United States Patent [19]

Tang et al.

[11] Patent Number: 5,066,772

[45] Date of Patent: Nov. 19, 1991

[54] MEDICAL DEVICES FABRICATED TOTALLY OR IN PART FROM COPOLYMERS OF RECURRING UNITS DERIVED FROM CYCLIC CARBONATES AND LACTIDES

[75] Inventors: Reginald T. Tang, Warren; Frank Mares, Whippany; William J. Boyle, Jr., Parsippany; Tin-Ho Chiu, Millburn; Kundan M. Patel, Landing, all of N.J.

[73] Assignee: Allied-Signal Inc., Morristown, N.J.

[21] Appl. No.: 467,067

[22] Filed: Jan. 18, 1990

Related U.S. Application Data

[60] Division of Ser. No. 226,706, Aug. 1, 1988, Pat. No. 4,916,193, which is a continuation-in-part of Ser. No. 134,321, Dec. 17, 1987, Pat. No. 4,891,263, and a continuation-in-part of Ser. No. 134,339, Dec. 17, 1987.

[51] Int. Cl.$^5$ ...................... C08G 63/64; C08G 63/62
[52] U.S. Cl. .................... 528/354; 528/370; 525/415; 604/366; 604/370; 604/372
[58] Field of Search ................. 528/354, 370

[56] References Cited

U.S. PATENT DOCUMENTS

| 3,639,503 | 2/1972 | Matzner | 525/413 |
| 4,300,565 | 11/1981 | Rosensaft et al. | 528/354 X |
| 4,429,080 | 1/1984 | Casey et al. | 528/354 X |
| 4,705,820 | 11/1987 | Wang et al. | 528/354 X |
| 4,711,241 | 12/1987 | Lehmann | 428/375 X |
| 4,716,203 | 12/1987 | Casey et al. | 528/370 X |
| 4,788,979 | 12/1988 | Jarrett et al. | 528/354 X |
| 4,791,929 | 12/1988 | Jarrett et al. | 528/354 X |
| 4,891,263 | 1/1990 | Kotliar et al. | 528/354 |

OTHER PUBLICATIONS

Chemical Abstracts 104, 10544k (1986).

Primary Examiner—John Kight, III
Assistant Examiner—Frederick Krass
Attorney, Agent, or Firm—R. C. Stewart, II; G. H. Fuchs; D. L. Webster

[57] ABSTRACT

This invention relates to novel copolymers containing carbonate repeat units and ester repeat units.

47 Claims, No Drawings

MEDICAL DEVICES FABRICATED TOTALLY OR IN PART FROM COPOLYMERS OF RECURRING UNITS DERIVED FROM CYCLIC CARBONATES AND LACTIDES

RELATED APPLICATIONS

This application is a divisional application of U.S. Pat. application Ser. No. 226,706, filed Aug. 1, 1988, now U.S. Pat. No. 4,916,193 which in turn is a continuation-in-part application of U.S. Pat. application Ser. No. 134,321 now U.S. Pat. No. 4,891,263 and U.S. Pat. application Ser. No. 134,339, each filed Dec. 17, 1987.

FIELD OF THE INVENTION

This invention relates to totally and partially bioresorbable devices capable of degrading into biologically innocuous components. More particularly, this invention relates to such devices which are fabricated totally or in part from copolymers having recurring units derived from cyclic carbonates and from lactides.

BACKGROUND OF INVENTION

Polycarbonates have been known for a number of years. U..S. Pat. No. 3,301,824 describes the preparation of carbonate homopolymers and random copolymers with cyclic lactones. While the patent generally discloses the polymers as having utility in the molding, coating, fiber and plasticizing fields, there is no appreciation whatsoever of biodegradable and/or bioresorbable devices composed in whole or in part of polycarbonate.

Non-bioresorbable synthetic permanent vascular grafts have been available and are made of either Dacron (polyethylene terephthalate) or microporous Teflon (polytetrafluoroethylene). Various prostheses such as grafts, and especially those of small diameters for use in coronary bypass procedures, must have certain properties. These properties include physical and mechanical compatibility with the vessel to which they are connected, suturability, compliancy, ability to withstand pressure and pressure fluctuations, and flexibility. Required properties also include biocompatibility, sterilizability, and low toxicity, allergenicity, and mutagenicity. Still other required properties include appropriate durability, both in terms of "shelf life" after fabrication and appropriate durability after implantation. Problems which arise from a mismatch of a native vessel and a prosthesis include dilatation which may result in aneurysm formation and anastomotic hyperplasia, kinking and the like. Vascular grafts having internal diameters of 8mm or more and made of biodurable materials have so far been the only successful prostheses for providing a conduit for maintaining continuous blood flow while inflicting a minimal hematologic trauma. Vascular grafts made of Dacron in current clinical use are constructed of knitted or woven Dacron fibers with open pores in the fabric which have to be closed or diminished by preclotting before implantation. Such prostheses have been used as vascular replacements, but only for the relatively larger arteries.

Bioresorbable polymers have been used in the fabrication of devices for implantation in living tissue for several decades. Medical application of such polymers include absorbable sutures, haemostatic aids and, recently, intraosseous implants and slow-release drug delivery systems, to name but a few. Use of such polymers has been extended to tissue regeneration devices such as nerve channels, vascular grafts, sperm ducts, fallopian tube ducts and the like. To be effective, these devices must be made from materials that meet a wide range of biological, physical and chemical prerequisites. The material must be bioresorbable at least in part, nontoxic, noncarcinogenic, nonantigenic, and must demonstrate favorable mechanical properties such as flexibility, suturability in some cases, and amenability to custom fabrication.

Various polymers have been proposed for use in the fabrication of bioresorbable medical devices. Examples of absorbable materials used in nerve repair include collagen as disclosed by D. G. Kline and G. J. Hayes, "The Use of a Resorbable Wrapper for Peripheral Nerve Repair, Experimental Studies in Chimpanzees", *J. Neurosurgery* 21, 737 (1964). *Artandi et al.*, U.S. Pat. No. 3,272,204 (1966) reports the use of collagen protheses that are reinforced with nonabsorbable fabrics. These articles are intended to be placed permanently in a human body. However, one of the disadvantages inherent with collagenous materials, whether utilized alone or in conjunction with biodurable materials, is their potential antigenicity.

Other biodegradable polymers of particular interest for medical implantation purposes are homopolymers and copolymers of glycolic acid and lactic acid. A nerve cuff in the form of a smooth, rigid tube has been fabricated from a copolymer of lactic and glycolic acids [*The Hand;* 10 (3) 259 (1978)]. European patent application 118-458-A discloses biodegradable materials used in organ protheses or artificial skin based on poly-L-lactic acid and/or poly-DL-lactic acid and polyester or polyether urethanes.

U.S. Pat. No. 4,481,353 discloses bioresorbable polyester polymers, and composites containing these polymers, that are also made up of alpha-hydroxy carboxylic acids, in conjunction with Krebs cycle dicarboxylic acids and aliphatic diols. These polyesters are useful in fabricating nerve guidance channels as well as other surgical articles such as sutures and ligatures.

U.S. Pat. Nos. 4,243,775 and 4,429,080 disclose the use of polycarbonate-containing polymers in certain medical applications, especially sutures, ligatures and haemostatic devices. However, this disclosure is clearly limited only to "AB" and "ABA" type block copolymers where only the "B" block contains poly(trimethylene carbonate) or a random copolymer of glycolide with trimethylene carbonate and the "A" block is necessarily limited to glycolide. In the copolymers of this patent, the dominant portion of the polymer is the glycolide component.

U.S. Pat. No. 4,157,437 discloses high molecular weight, fiber-forming crystalline copolymers of lactide and glycolide which are disclosed as useful in the preparation of absorbable surgical sutures. The copolymers of this patent contain from about 50 to 75 wt. % of recurring units derived from glycolide.

SUMMARY OF THE INVENTION

The present invention relates to a bioresorbable or biodurable medical device fabricated totally or in part from a copolymer selected from the group consisting of copolymers having at least one type of recurring monomeric units of the Structure I:

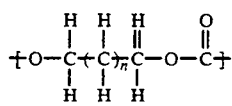

Structure I and having at least one type of recurring monomeric unit of the Structure II:

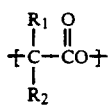

Structure II wherein:

n is from 1 to about 8: and $R_1$ and $R_2$ are the same or different and are hydrogen, alkyl or phenyl with the proviso that when said copolymers are block copolymers at least one of $R_1$ and $R_2$ is other than hydrogen.

The copolymers used in the practice of this invention exhibit various physical and morphological properties which enable their use in the fabrication of a large number of medical devices. The copolymers for use in the practice of this invention may be crystalline to semi-crystalline to amorphous having varying modulus and tensile strength, elasticity, pliability and bioresorption rates. The device may be implanted in humans to aid in tissue regeneration, growth and/or healing, or may be used outside of the body but in contact with living tissue, bodily fluids and/or blood without undue adverse impact on such tissue, fluids and/or blood. For example, copolymers used in the practice of this invention are amorphous, soft and pliable materials having relatively fast rates of bioresorbability which can be fabricated into solid medical devices, thin films, coatings and the like where softness and pliability are necessary requirements for the efficacy of the device. Other copolymers used in this invention are elastomeric which allow their use in the fabrication of elastic fibers and medical devices, coatings, films and the like where certain elasticity is critical for efficacy. Still other of the copolymers of this invention are crystalline which exhibit high modulus, high tensile strength, and relatively slow rate of bioresorption. These copolymers can be conveniently fabricated into medical devices and fibers where high strength and relatively slow rate of bioresorption are critical.

The copolymers for use in the fabrication of the device of this invention exhibit controllable bioresorbability and biodegradation rates, blood compatability, and biocompatibility with living tissue. These copolymers also induce minimal inflammatory tissue reaction. The biodegradation of the copolymers used to fabricate most of the biodegradable devices of this invention usually results in degradation products having a physiologically neutral or relatively neutral pH. Various properties of the copolymers used in the practice of this invention render devices made from the copolymers especially suitable for medical applications including but not limited to fabrication of the bioresorbable medical devices, such as vascular grafts, coating and films, wound and skin covers, hemostatic aids, bone or dental repair, and the like.

As used herein, "biodurable" means that the device is substantially not biodegradable or bioresorbable.

As used herein, "living system" is a living cell, animal or plant, whatever phylogenetic level in the plant or animal kingdom.

As used herein, "biologically innocuous components" are components which may be contacted or implanted into living systems without inducing an adverse reaction and/or components which may be metabolized by the living systems.

As used herein, the term "biodegradable" means capable of being acted upon biochemically in general by living cells or organisms or part of these systems, including water, and broken down into chemical or biochemical products.

As used herein, "medical device" is a device used within or without a human body or animal body to achieve certain medical benefits of goals.

As used herein, "bioresorbable" is capable of being broken down and metabolized by a living system.

As used herein, the term "copolymer" is a homopolymer and/or copolymer collectively.

As used herein, "biocompatible" is the capability to exist or coexist inside or in close contact with the living systems without adversely impacting the system.

DETAILED DESCRIPTION OF THE INVENTION

This invention is directed to medical devices. The medical devices of this invention may be totally or partially bioresorbable and/or biodegradable or may be biodurable. The devices of the invention are fabricated totally or in part of at least one copolymer of this invention or a combination thereof. The device may be formed totally out of the copolymer of this invention, or may be formed partially of the copolymer of this invention in which the body of the device is formed of one or more other biodurable or bioresorbable materials coated with the copolymers of this invention using such techniques as solution dipping and solution coating, or the device may be a layered device in which one or more layers are formed from the copolymers of this invention. The only requirement is that the device is fabricated wholly or partially from at least one copolymer comprising at least one type of recurring monomeric unit of each of Structures I and II.

The devices of this invention may take many forms and have varying degrees of bioresorbability and/or biodegradability, depending on intended use. For example, the devices of this invention may be solid articles fabricated using conventional techniques for fabricating parts from thermoplastic polymers such as injection molding, melt extrusion, solution casting, solution extrusion, gel extrusion and the like, such as an extruded hollow tubular nerve channel or extruded hollow vascular graft, or a stent for use in angoplasty. The devices of this invention may also be fibrous devices constructed of woven or non-woven fabric made of fibers formed from the copolymers of this invention. For example, the device of this invention may be fabricated from fibers and/or yarns which have been woven, braided and/or knitted into fabrics having various structural configurations using conventional means, which fabrics may then be used to fabricate a device, such as a wound cover, gauze, and a vascular graft coated with one or more copolymers of this invention.

Illustrative of useful devices of this invention are orthopedic and fracture fixation devices such as pins, clamps, screws, rods, maxillo facial repair implants, intraosseous implants, and plates: vascular implants such as vascular grafts and vascular stents; wound closing device such as sutures, fasteners, clips and staples: nerve channels: and the like. Illustrative of still other devices within the scope of this invention are devices for tendon and ligament replacement, breast prostheses, wound and burn dressings, dental packs, sponges, hernia patches, absorbant swabs, fallopian tube and sperm ducts, drug-delivery devices, and the like The rate of bioresorption and/or biodegradation exhibited by the device of this invention will vary depending on the desired longevity of the device. For example, because of the relatively high degree of compatibility between the copolymers used in the construction of the device of this invention and blood and tissue of living systems, one device of this invention is a conventional part which contacts blood, other bodily fluids, or living tissue such as tubing of an extracorporeal loop or other types of flow-through systems for blood, bodily fluids, heart valves and the like. In such instances, the device should be formed or at least have a surface which will contact the blood, bodily fluids, and/or the living tissue coated with a copolymer having a relatively slow rate of bioresorbability and/or biodegradeability or which is even relatively biodurable. On the other hand, another device of this invention is a vascular graft composed of a fabric composed of a relatively biodurable material such as Dacron or a bioresorbable copolymer having a relatively slow rate of bioresorption coated with a relatively fast bioresorbing copolymer, especially in the inside of the graft. The use of the coating having fast rate of bioresorption provides for a regenerated blood vessel having a high degree of patency and relatively low rate of thrombosis.

In one preferred embodiment of this invention, the devices are composed of solid articles which are fabricated from the copolymers through use of conventional techniques such as injection molding, gel or melt extrusion and the like for fabricating solid articles from thermoplastic polymers. These techniques are well known in the art and will not be described herein in any great detail. For example, such techniques are described in Encyclopedia of Polymer Science and Technology InterScience, N.Y. The preferred solid devices of this invention are relatively biodurable tubing and coatings which will contact the blood or tissue of a living system, biresorbable and/or biodegradable orthopedic pins, rods and plates, extruded wound and burn coverings, extruded nerve growth channels, extruded fibers for use in tendon and ligament repair and the like.

In another preferred embodiment of the invention, the devices are fibrous devices fabricated totally from fibers composed of the copolymers of this invention. The fibers, which are also devices of this invention, are prepared by any suitable fiber-forming technique, and the fibers can then be fabricated into useful medical devices using conventional techniques. For example, fibers made from the copolymers may be formed by conventional processes such as spinning techniques, including melt, solution, dry and gel spinning. Illustrative of suitable fiber spinning processes and melt spinning techniques and apparatus for carrying out these processes are those described in "Man Made Fibers Science and Technology", Vol. 1-3, H. F. Mark et al., Interscience New York, 1968: "Encyclopedia of Polymer Science and Technology", Vol 3; Fundamentals of Fiber Formation by Androzej Ziabuke, Wiley and Sons, New York, N.Y. (1976); and "Encyclopedia of Polymer Science and Technology", Vol. 3, pps. 326-381.

Preferred implantable bioresorbable medical devices are vascular implants, nerve channels; burn and wound covers; facial substitutes; orthopedic substitutes for bone or bone repair; breast prostheses; tendon and ligament replacements; hernia patches; and the like, or used as sutures and fasteners. Other devices not necessary for implantation purposes can also be formed from the fibers of this invention. The devices include cell culture substrates, absorbants or swabs, medicated dressings, gauze, fabric, sheet, felt or sponge for hemostasis, dental packs and the like. Particularly useful devices are woven or knitted fabrics formed into tubes of varying shapes, lengths and diameters. Illustrative of these devices are tubular prostheses such as vascular grafts, nerve guidance channels and the like. The particular configuration of such tubes may vary according to the size and shape of the organ to be repaired, and whether the intended repair is to take place in human surgery or in surgery involving other animal species.

Other preferred devices of this invention are those which are useful in ligament and tendon replacements. These devices are usually constructed of a fiber-like body composed of a relatively biodurable material such as ceramic fibers, graphite, polyethylene and the like coated with a bioresorbable or biodegradable copolymer. Organized tissue formation is encouraged by the use of the composites of this invention, which aids in regenerating ligaments and tendons.

Yet other preferred devices of the invention are those which are useful in dental and orthopedic repair. In this application, the dental and orthopedic repair devices may be used in composite structures with or without such materials as calcium hydroxyapatite, glassy calcium phosphate, Bioglass, calcium triphosphate, drugs, and the like.

Still other preferred embodiments are devices for use as drug delivery system. Such drugs include drugs for control of body functions such as birth control and other medicinal drugs. In these embodiments, the drug can be dispersed in a bioresorbable copolymer matrix having a bioresorption rate such that the desired quantity of drug is released into body as a function of time.

Other preferred devices of this invention are hollow fibers which are particularly suited for use as nerve channels for the repair of severed nerves formed from the copolymers by any conventional technique such as solution dipping on a mandrel, melt extrusion, solution extrusion, gel extrusion, and the like. The diameters of the nerve channels will vary according to the size and shape of the nerve to be repaired U.S. Pat. No. 3,833,002 discloses various sizes and shapes that may be employed. Lengths of the hollow fibers or tubes and their internal diameters and wall thicknesses will also vary according to intended use. The length of the hollow fiber or tube is usually sufficient to bridge the size of the gap to be repaired and to allow extra tubing in which to insert nerve stumps. Particularly useful internal diameters commonly range from about 0.13 mm to about 5.00 mm. Particularly useful wall thicknesses are usually from about 0.01 mm to about 3.0 mm, and preferably from about 0.05 mm to about 1.5 mm.

The devices of this invention are fabricated totally or in part from copolymers having at least one type of recurring monomeric unit of the Structure I:

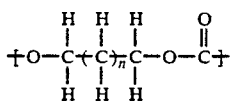

Structure I and at least one type of recurring monomeric unit of the Structure II:

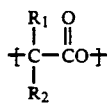

Structure II wherein $R_1$, $R_2$, and n are as described above.

Illustrative of recurring monomeric units of the Structure I are trimethylene carbonate, tetramethylene carbonate, pentamethylene carbonate, hexamethylene carbonat and the like. Illustrative of recurring monomeric units of the Structure II are those derived from substituted and unsubstituted dilactones such as those of the formula:

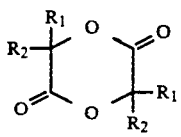

wherein $R_1$ and $R_2$ are as described above. Such dilactones include lactides such as l-lactide, d-lactide, and d,l-lactide and lactones and dilactones such as those derived from 2-hydroxycarboxylic acids such as 2-hydroxybutyric acid, 2-hydroxy-2-phenylpropanoic acid, 2-hydroxy-4-methylpentanoic acid, 2-hydroxyhexanoic acid, 2-hydroxyoctanoic acid, and the like.

Preferred for use in the practice of this invention are devices formed totally or in part from copolymers formed from at least one type of recurring unit of the Structure I wherein:

n is 1, 2, 3, 4 or 5: and where monomeric units of the Structure II are derived from l-lactide, d,l-lactide, d-lactide, 2-hydroxybutyric acid or 2-hydroxy-2-phenylpropanoic acid.

In the most preferred embodiments of this invention, the device is formed totally or in part from copolymers comprising at least one type of recurring monomeric unit of the Structure I:

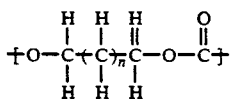

Structure I wherein
n is 1, 2 or 3 and comprising at least one type of recurring monomeric units of the Structure II derived from l-lactide, d,l-lactide or d-lactide.

Copolymers for use in the fabrication of the device of this invention can be random copolymers or may be block copolymers depending on the properties of the polymer required for the particular application. Illustrative of useful copolymers are random copolymers comprising one or more monomeric units of each of the Structures I or II. Also illustrative of copolymers useful in the fabrication of the device of this invention are block copolymers comprising one or more "B" blocks which may be formed of recurring units of Structure I and one or more "A" blocks which may be formed from one or more recurring units of Structure II. Each "A" block and each "B" block may be the same or different. As used herein, the term "block" means a sequence of one type of monomeric unit at least about 5 monomeric units long, or such sequence of two or more types of recurring monomeric units either randomly distributed in such a sequence or distributed such sequence in a block-like fashion. Each "A" block and "B" block may comprise a single type of recurring monomeric unit. Alternatively, each block may comprise more than one type of recurring monomeric unit, randomly distributed throughout each block. For example, the block copolymers as described above may have repeating block units such as AB, ABA, BAB, ABAB, ABABA, BABAB, and the like, where each "A" block and each "B" block contains the same or substantially the same types of recurring monomeric unit, and/or where each block contains the same or substantially the same number of recurring units. Alternatively, the various "A" and "B" blocks contained in the block copolymers may have more than one type of "A" block or "B" block, each of which may contain a different type or types of recurring monomeric units; or each block may contain the same or different types of recurring units but have differing number of recurring units in each block. With respect to the recurring blocks of A's and B's, each of them may also be the same or different. For example, ABABA may in fact be MNOPQ, ABA may be MNQ or ABA may be MNOPQ, where M, N, O, P and Q are the same or different provided that at least one of M, N, O, P and Q is a recurring unit of the Structure I or II.

In some preferred embodiments of this invention where soft, pliable and relatively fast bioresorbing materials are required as for example in coatings and the like, the polymer of choice is a random copolymer. In other preferred embodiments of this invention where hard, crystalline and relatively slow bioresorbing materials are required as for example orthopedic and fracture-fixation devices, the copolymers of choice are block copolymers. Especially preferred are block copolymers of structures AB and ABA, with ABA being the most preferred. Through use of selected monomeric units and their arrangement in the polymer chain, thermal history, mechanical processing and treatment of the copolymer and the devices fabricated from the devices, the properties of the copolymer such as elasticity, modulus, pliability, hardness, softness and crystallinity, and the bioresorption rate of the copolymer can be tailored and optimized for any particular application.

The types of recurring monomeric units and molecular weight of the copolymer, as well as the relative percentages of each of the recurring monomeric units in the copolymers used in the fabrication of the device of the invention may vary widely depending on the particular device and the desired characteristics of the copolymer or homopolymer. The types and quantities of recurring units and the molecular weight impact on the physical properties of the copolymer such as tensile strength, modulus, hardness, elasticity, softness, toughness, compliancy, crystallinity, bioresorption rate and the like as needed for optimized or at least acceptable performance of the device. These properties in turn, will be determinative of the characteristics of the device and the suitability and efficacy for use in any application. Various types and amounts of recurring monomeric units can be conveniently selected to tailor the properties of the copolymer to optimize the desirable properties required for any device.

While we do not wish to be bound by any theory, it is believed that whether it is random or block copolymers, the higher the content of monomeric units of the Structure I the more flexible and soft the copolymer will be. Conversely, in such random or block copolymers, the higher the content of monomeric units of the Structure II, the more crystalline and hard the copolymer. With respect to biodegradation or bioresorption, the higher the crystallinity, the slower the rate of bioresorption or degradation. For example, soft, pliable and relatively fast bioresorbing coatings and devices can be obtained from a 90:10 random copolymer or trimethylene carbonate and lactide and 95:5 block copolymer or trimethylene carbonate and lactide. In other situations where toughness and a slower bioresorption rate is desired as for example in a stent, a tendon or ligament replacement device, orthopedic plates and pins, monomeric units such as those of the Structure II are selected and incorporated into the copolymer in a major amount. For example, hard and crystalline devices can be obtained from a 85:15 block copolymer l-lactide/trimethylene carbonate/l-lactide.

The preferred embodiments of this invention where the desired material is soft, pliable and relatively fast bioresorbing recurring units of the Structure I are in the "major amount". As used herein, "major amount" is more than about 50 weight % based on the total weight of all recurring monomeric units in the copolymer. In the preferred embodiments of the invention, the amount of recurring units of Structure I may range from greater than about 50 wt. % to less than about 100 wt. %, based on the total weight of recurring units in the copolymer, preferably from about 80 wt. % to less than about 100 wt. %, and most preferably from about 90 wt. % to about 99 wt. %.

The preferred embodiments of this invention where the desired material is hard, crystalline and relatively slow bioresorbing recurring units of the Structure II are in the "major amount". As used herein, "major amount" is more than about 50 weight % based on the total weight of all recurring monomeric units in the copolymer. In the preferred embodiments of the invention, the amount of recurring units of Structure II may range from greater than about 50 wt. % to less than about 100 wt. %, based on the total weight of recurring units in the copolymer, preferably from about 80 wt. % to less than about 100 wt. %, and most preferably from about 90 wt. % to about 99 wt. %.

Useful average molecular weight ranges of copolymers for use in any particular situation will vary depending on the desired characteristics of the copolymer. In general, physical properties such as modulus, tensile strength, crystallinity and the like require a certain minimum molecular weight, which will vary with each copolymer. Above this minimum, the properties do not depend strongly on molecular weight. Melt viscosity and solution viscosity increase with increasing molecular weight useful for a particular polymer. For this reason, there usually will be a maximum molecular weight because of the difficulty of processing it into the desired articles by conventional technology. Within the range of useful molecular weights, the rate of bioresorption will vary with the molecular weight and the crystallinity of the copolymer. Higher molecular weight and more crystalline copolymers will require longer times to bioresorb. The desired length of duration of the device will bioresorb will dictate the choice of molecular weight.

In general, the devices of this invention are formed totally or in part of copolymers having at least one type of recurring monomeric units of Structure I and II that can range in molecular weight from low molecular weight to extremely high molecular weight. Molecular weights of copolymers for use in the practice of this invention usually are equal to or greater than about 3,000. Preferred average molecular weight ranges are from about 7,000 to about 5,000,000, with a range of from about 10,000 to about 500,000 being particularly preferred, and a range of from about 15,000 to about 250,000 being most preferred.

Other components may be combined with the copolymers before they are formed into the devices of the invention, or added to, coated onto and the like, during or after their formation. These components include substances that will not interfere with the desired properties of the copolymers, e.g., their ability to degrade into components biologically innocuous to living systems. Among the contemplated classes of such substances are placticizers, stabilizers for UV or temperature, pigments, lubricants and antioxidants. One of skill in the art will appreciate that any additives included in the medical devices of the invention, should be those that would meet with FDA approval.

Other optional polymeric components, either bioresorbable or biodurable, such as fibers, fillers and binders may be combined with the copolymers prior to and during the formation the devices, or subsequent to their formation. These include, but are not limited to polymers and copolymers selected from the group consisting of polyesters such as poly(butylene terephthalate) and poly(ethylene terephthalate); poly(vinyl alcohol); poly(vinyl acetate) and partially hydrolyzed forms thereof; hydrogel type polymers such as poly(hydroxyethyl methacrylate), poly(hydroxypropyl methacrylate), and the like; polysulfones such as poly(phenylenesulfone); carbon; silicon carbide; halopolymers such as poly(tetrafluoroethylene), ethylene/tetrafluoroethylene copolymer and the like; poly(dioxanone); poly(glycolide-co-trimethylene carbonates); poly(lactides); poly(d-lactide); poly(l-lactide); poly(lactide-co-caprolactone); poly(d,l-lactide); poly(caprolactones); poly(hydroxybutyrates); poly(hydroxyvalerates); poly(hydroxybutyrate-co-hydroxyvalerates); poly(glycolide); poly(urethanes); segmented poly(urethanes); poly(etherurethanes); poly(urethane ureas); silicone rubber; and substances such as fibrin and its powder; natural or processed collagen; mono-, di-, tri-, and poly(saccharides); poly(ethylenes); poly(amides); poly(propylene); peptides such as nerve growth factors, bone growth factors, laminin, and the like; poly(carbonates); poly(vinyl fluoride); poly(vinylidene fluoride); poly(vinyl butyral); cellulose such as, carboxylmethyl cellulose, cellulose acetate, ethylcellulose, and the like; ethylene vinylacetate copolymers and hydrolyzed and partially hydrolyzed forms thereof; poly(acrylonitrile); poly(vinyl methyl ether); and their derivative copolymers, blends, composites, and the like.

Other biocompatible components besides polymeric components may be combined with the polymers during or before they are formed into the devices of the invention, or added to, coated onto and the like, after their formation. These components include substances that will enhance certain of the desired properties of devices made from the copolymers. Illustrative of such substances are plasticizers, lubricants, antioxidants, stabilizers of all kinds such as stabilizers for UV radiation, heat, moisture, and the like, as well as drugs for treatment of certain disorders or diseases and growth factors such as those for nerve, bone, and growth hormones in general. Materials such as calcium phosphates, ceramics, bioresorbable or otherwise, such as calcium hydroxyapatite, Bioglass, and calcium triphosphate may also be combined with the polymer. Components such as certain barium salts to render devices formed with them radio-opaque are also within the contemplation of the invention. Certain of these fillers, binders, additives and components can be removed or leached from such copolymers contained in the devices at some stage, so that a porous or semi-porous system can be obtained.

The devices of this invention may also include other bioresorbable materials. Illustrative of such materials are those described in U.S. Pat. Nos. 4,052,988; 4,157,437; 4,190,720; and ,429,080 and the materials described in U.S. Pat. application Ser. Nos. 134,321, filed Dec. 17, 1987 and 134,339, filed Dec. 17, 1987.

Devices of this invention may be fabricated totally from the copolymers of the Structure I or II or may be fabricated in part from other bioresorbable materials or from biodurable materials which are relatively resistant to biodegradation. Illustrative of biodurable materials useful in the fabrication of devices of this invention are silicone, silicone rubber, poly(ethylene), poly(ethylene terephthalate), poly(fluoroethylene), poly(phosphazene), poly(urethane), segmented poly(urethane), and the like. Also useful are biodurable metallic substances such as titanium, stainless steel, and alloys such as chrominium-cobalt-molybelenum alloys, titanium-aluminum-vanadium alloys, and the like.

The following are more specific examples of various embodiments of the invention and are not to be considered limitative thereof.

EXAMPLE 1

Synthesis of 1,3-Dioxan-2-one (Trimethylene Carbonate (TMC))

A 1-liter three-neck round bottom flask was fitted with mechanical stirrer and a 12 in. Vigreux column topped with a distilling head having a stopcock for controlling the reflux ratio. The flask was charged with 1,3-propanediol (228.3 g, 3 mol) and diethyl carbonate (454 mL, 3.75 mol), flushed with nitrogen, then immersed in an oil bath. Heating was initiated and, when the temperature had reached about 80° C., sodium methoxide (1.62 g, 30 mmol) was added via funnel through the third neck. The oil temperature was raised to 155°-160° C., and ethanol soon began to reflux.

Ethanol was removed gradually over a period of about 3.5 hrs. under partial reflux. Takeoff cannot be too fast, as the temperature rises from about 80° C. as the distillate becomes rich in diethyl carbonate. A total of 268 grams of distillate was collected, with about 80-85% ethanol and the remainder carbonate by NMR. Additional sodium methoxide (0.40 g, 7.4 mmol) was cautiously added at this point and heating was continued for another 30 mins. A slight vacuum was carefully applied, and additional distillate collected. The vacuum was gradually increased until the pressure was down to about 1 mm, by which time most of the remaining diethyl carbonate was removed.

The oil bath was lowered and stirring continued for about 15 min. (temperature was not monitored). Triethylamine hydrochloride (5.2 g, 38 mmol) was added and stirring continued for 45 min. without heating. Stannous octoate (15 drops, about 0.2 grams) was added, heating resumed (bath at 150° C. initially, increasing to 200° C.), and a vacuum gradually applied to about 0.5 mm. An initial forecut boiling 70°-125° C. (25 g) was rejected, while the main fraction (245 g) collected at 125°-135 ° C. (0,5 mm) was about 85% pure by NMR. The residue from the distillation was dissolved in chloroform, filtered and distilled in a Kugelrohr at 160°-220° C. (0.1 mm) to give an additional 25 grams of dioxanone.

The main fraction was recrystallized from 1:1 ether: THF (4 mL/g) to give 168 g of dioxanone of high purity. Evaporation of the filtrate and trituration with ether-THF (about 4:1) gave an additional 45 g of crude product, which was combined with the 25 grams obtained from cracking of the residue. Recrystallization from ether-THF gave 46.5 g of pure dioxanone. The combined 214.5 grams of dioxanone was distilled in the Kugelrohr at 120°-130° C. (0.1 mm) to give 209.3 g (68% of theory) polymer grade product.

EXAMPLE 2

Poly (TMC-co-1-Lactide)

Freshly distilled trimethylene carbonate (12.95 g, 127 mmol) was melted together with dried, recrystallized 1-lactide (2.03 g, 14.1 mmol), then the mixture was syringed into a 15 mL polymerization tube. The catalyst (73 $\mu$L of $3.0 \times 10^{-2}$M. stannous octoate in toluene) was added, then the tube was degassed by freezing, pumping and thawing twice. After sealing under vacuum, the tube was immersed in an oil bath at 160° C. for 60 hours. The tube was cracked and 10 g of the crude polymer was dissolved in chloroform (250 mL), then precipitated into isopropanol. The dried polymer, 8.6 g, had a reduced viscosity of 1.53 dL/g (0.1% solution in dioxane).

In another experiment, freshly distilled trimethylene carbonate (12.95 g), 2.03 grams of recrystallized L-lactide and 7.5 $\mu$L of 1.0M. stannous octoate in toluene was placed inside a 160° C. oil bath for 16 hrs. The ampule was cracked and 12.9 grams was the final yield after twice reprecipitated from tetrahydrofuran (THF) solution. The weight average molecular weight was 87,000 and number average molecular weight was 13,760 by GPC in THF. The GPC system was calibrated with polystyrene standards.

EXAMPLE 3

ABA Block Copolymer of Trimethylene Carbonate (TMC), d,1-lactic Acid (d,1-LA) and 1-lactic Acid (1-LA)

An oven-dried, silanized glass 100 mL resin flask was equipped with mechanical stirrer and a glass paddle, argon inlet, a serum cap on one port, and a glass stopper on the remaining port. To the flask were added freshly dried and purified TMC (19.80 g, 194 mmol), d-1-Lactide (2.20 g, 15.3 mmol), and 2,2-dimethyl-1-3-propanediol (27 mg, 0.26 mmol). The flask was evacuated and filled with argon several times, then immersed in an oil bath at 150° C. Stirring was initiated, and after 5 minutes, 40 $\mu$L of a 1.0M solution of stannous octoate in toluene was added.

After one hour, a sample of the viscous polymer was removed and 1-Lactide (9.43 g, 65.4 mmol) was added through one port. Stirring was stopped after one hr., then heating stopped after an additional hr. The polymer was removed from the flask, dissolved in tetrahydrofuran (250 mL), precipitated into methanol (750 mL), and dried under vacuum at 50° C. Yield: 23.2 g (74%). Weight average molecular weight (relative to polysytrene standards) of the prepolymer=57,000; of the final polymer=107,000. Proton NMR analysis of the final polymer shows a TMC content of 50 mole percent (theoretical=55%). From the methine region of the proton NMR, one can estimate that about 74% of the lactic acid units are connected to other lactic acid units, compared to a theoretical value of 89.5% for a totally random B block and a totally homopolymer A block.

Similarly, two experiments were performed using this method to prepare other such block copolymers:

by 120 picks per inch (that is a perfect square, tight weave). The total circumferences were 18.8 and 25.2 mm for each of the fibers used, which correspond to 6 to 8 mm diameter respectively. Some obviously defective areas were found from time to time due to slight changes of tension on the fill bobbin, and also due to the knots in the towed fiber.

3. Crimping according to the general method of Jekel (U.S. Pat. No. 3,337,673) was used. Thus, the spacer was provided by a cotton string helically wound on the fabric graft body with a glass mandrel inserted into the lumen. Crimp-shape was formed by slowly forcing the two ends of the graft towards the middle. The crimping can be set to as small as 0.5 millimeter up and 0.1 to 0.2 mm down so that the internal surface appears to be

| ABA BLOCK COPOLYMERS OF TRIMETHYLENE CARBONATE (TMC), d, l-lactic acid (d, l-LA) and l-lactic acid (l-LA) | | | | | |
|---|---|---|---|---|---|
| Sample No. | A Block | B Block | A:B Ratio | Quantity Isolated | Yield (%) |
| 1 | l-LA | TMC:d, l-LA 9:1 | 30:70 | 21.2 g | 78 |
| 2 | l-LA | TMC:d, l-LA 7.3:1 | 36:64 | 22.0 g | 72 |
| 3 | l-LA | TMC:d, l-LA 1:1 | 33:67 | 19.8 g | 80 |

| Sample No. | GPC Main Peak | | GPC Overall | | $T_g$ | $T_m$ | % TMC by NMR (Theory) |
|---|---|---|---|---|---|---|---|
| | Wt Av MW | Disp. | Wt Av Mw | Disp | | | |
| 1 | 94,000 | 2.64 | 120,900 | 24.8 | −5° C. | 150° C. | 63 (63) |
| 2 | 86,800 | 1.72 | 80,800 | 1.72 | −10° C. | 156° C. | 56 (55) |
| 3 | 50,000 | 3.60 | 68,000 | 16.0 | 17° C. | 124° C. | 31 (33) |

EXAMPLE 4

Trimethylene Carbonate/1-Lactide [90/10] Random Copolymer.

In a 100 mL reaction flask fitted with mechanical stirrer and argon inlet were combined trimethylene carbonate (51.45 g, 504 mmol), 1-lactide (8.07 g, 56 mmol), and 1,6-hexanediol (47 mg, 0.40 mmol). The flask was evacuated and filled with argon several times, immersed in an oil bath at 160° C. and stirring was initiated. After 10 mins., the polymerization catalyst, 25 μL of 0.20M solution of tin(II) octoate in toluene, was added via syringe. The mixture was stirred at 160° C. for 4 hrs., then the polymer was removed from the flask, dissolved in tetrahydrofuran (450 mL), and precipitated into methanol (1200 mL) in a blender. The precipitated polymer was stirred with additional methanol (400 mL) in the blender, filtered, and dried in the vacuum oven at 50° C. Yield: 43.8 g (74%). Weight average molecular weight=120,000 (polydispersity 1.5). Proton NMR (400 MHz) shows a final composition of 80% trimethylene carbonate units and 20% lactic acid units (theoretical 82% and 18%, respectively). This polymer is especially useful as a coating polymer.

EXAMPLE 5

Completely Bioresorbable Crimped and Coated Graft:

1. Totally bioresorbable 6 mm vascular grafts were woven from fibers of random copolymers of 97.5% 2,2-dimethyltrimethylene carbonate (DMTMC) and 2.5% TMC, and from fibers of random copolymers of 98.2% DMTMC and 1.8% caprolactone.

2. Weaving: The 200 denier fiber was twisted 7.125 turn/inch when repackaged, to be used for the filling (horizontal) and wrap (vertical) construction to keep the monofilaments together. The fabrics were a plain weave tube with both warp and fill directions having the same fiber, at a construction of 120 total body ends almost smooth but still resist kinking. After heat-setting, cleaning was done according to section 4 of Example 29.

4. A solution containing 2 to 3% coating polymer, e.g., the random copolymer of 91% TMC—9% 1-lactide, was made with solvent dimethyl sulfoxide (DMSO). The clean bioresorbable graft was dipped into said solution six dips, inverting between each dip, to yield a 10% weight gain. In another example, when a 4.5% coating solution was used, 25% weight gain was obtained after nine dips. The dipping was performed inside a Class 100 laminar flow hood.

5. Standard room temperature cycle ethylene oxide was used to sterilize these completely bioresorbable coated and crimped vascular grafts.

6. The water permeation rates at 120 mm Hg pressure of such prostheses were about 400cc/cm$^2$-minute. They were implanted bilaterally in sheep as carotid replacements without preclotting. No complication resulted. The patency rate at 12-week stands at 100% (6 out of 6 grafts) for these 6 mm, totally bioresorbable, crimped and coated vascular grafts.

EXAMPLE 6

Eight 8 centimeter long pieces of human-implantable grade, crimped USCI Sauvage Bionit, vascular grafts manufactured by C. R. Bard, having a six millimeter diameter, were ultrasonicated with 0.05% Triton X-100 in 1:1 alcohol/water for sixty minutes at room temperature. The vascular protheses were then rinsed several times with deionized water, followed by two rinses with 95% ethanol and drying in a laminar blow hood equipped with high efficiency air filters. The dried vascular grafts were immersed into a solution of 1.40 grams of double-precipitated random copolymer of 91% TMC-9% 1-lactide (approx. 87,000 Daltons weight average molecular weight) in 140 mL of tetrahydrofuran, THF. The vascular grafts were inverted after each dip, allowed to dry, and weighed until the desirable weight gains were attained. A total of seven dips were performed for a 25% weight-gain. The dipping and packaging were performed inside the laminar flow hood. The protheses were subjected to room temperature ethylene oxide sterilization. The water permeation rate decreased from 1,500 to below 200 cc/cm$^2$ min. after the decrease coating.

Under anethesia, light anticoagulation (during implantation) and sterile operating room conditions, two vascular grafts were implanted by end-to-end anastomoses without preclotting into both the left and right external carotid arteries of each of the four adult domestic female sheep weighing approx. 50 kilograms.

After seven weeks, one of the four sheep was electively terminated and both grafts were patent and displayed pearl-like neointimal surfaces. The remaining three animals were kept to twelve weeks and electively terminated so as to be able to be compared to the control described in Example 31. All six excised grafts were patent and the blood contacting surfaces displayed smooth translucent pseudoneointimal layers.

Control Experiment. For comparison, the same procedure was performed with the Sauvage Bionit graft as received without coating. However, the grafts were preclotted just prior to insertion, a standard procedure used to diminish bleeding as suggested by the manufacturer. The patency rate was 15 out of 18 (83.33%). All luminar surfaces of the implants were covered with a much thicker layer of internal capsule and red thrombus as compared to the coated grafts described above.

EXAMPLE 7

Similar to Example 6, four similar eight centimeter long six millimeter diameter Sauvage Bionit vascular graft with the same coating polymer but 50% weight gain were implanted in two adult sheep as bilateral carotid replacements. One was electively terminated at seven weeks and the other at twelve weeks. All four excised grafts were patent at termination with pearl-like blood contacting surfaces.

EXAMPLE 8

Fibers obtained from a random copolymer of 97.5% DMTMC and 2.5% TMC were towed to 180 denier and woven into six millimeter tubular fabric with 120 body ends per inch by 120 picks per inch. The fabric was crimped by first wrapping a cotton thread spirally around the tubular fabric supported with a pyrex glass rod as a mendrel, then compressed and heat-set at approx. 80° C. The experimental grafts were cleaned as previously described. The grafts were further coated with the random copolymer of 91% TMC and 9% L-lactide from a 2 wt % solution in dimethylsulfoxide which dissolved the coating copolymer but not the fabric fiber. The water permeation rates dropped from 300 cc/cm$^2$ min. to about zero after coating. A total of fourteen eight centimeter long six millimeter diameter completely bioresorbable vascular grafts, crimped and coated with 10% wt-gain, were implanted as bilateral carotid replacements in adult sheep as described in Example 6. One sheep died acutely (never recovered from anesthesia) for reasons unrelated to the grafts, as both grafts and the suture-lines were all intact. Five animals were kept to twelve weeks post operation and electively terminated. All ten excised vascular grafts were patent. The last animal was electively terminated after 24 weeks and both of the excised grafts were patent.

EXAMPLE 9

As in Example 8, six mm diameter vascular grafts were woven from yarns extruded from random copolymer with 95.6% DMTMC and 4.4% caprolactone. It was crimped, cleaned, coated and sterilized as described. A pair of such grafts, with 10% coating (copolymer of 91% TMC and 9% L-lactide) were implanted under sterile conditions, as described, into an adult sheep as bilateral carotid replacements. After eight weeks indwelling, the animal was electively terminated and the excised grafts were patent and the neointimal surfaces were thin and pearl-like.

EXAMPLE 10

Six Weavenit Dacron (Meadox Medical), crimped human implantable vascular grafts (4 mm diameter, 4 cm in length) were coated to 10% weight-gain with random copolymer of 91% TMC and 9% L-lactide in tetrahydrofuran solution. Water permeation rate dropped from 1,500 cc/cm$^2$min. to 175 cc/cm$^2$min when coating was equal to 10% of the initial weight. The leak rate was considered to be tolerable without preclotting. After sterilization, they were implanted as carotid replacements in three mongrel dogs weighing approximately 22 kilograms each. Each dog received dipyridamole (25 mg) and aspirin (325 mg) beginning at 4 days preoperatively and continued for 2 weeks postoperatively so as to minimize the effect of sugery. All three animals were electively terminated at 4 weeks postoperatively (i.e., the subjects were with antiplatelet treatment for two weeks followed by two without such treatment). Four of the six grafts were found to be patent.

EXAMPLE 11

Similar to Example 10, four such Weavenit four millimeter diameter grafts were coated with the copolymer of 91% TMC and 9% L-lactide to 25% weight-gain. The water leakage rate dropped from 1500 cc/cm$^2$ min to almost zero. The grafts were implanted into two mongrel dogs given the same antiplatelet treatment for the pre- and post-operative periods. At four weeks post-operation, both animals were electively terminated and the four excised grafts were found to be patent.

EXAMPLE 12

Suture Fabrication

1. Using a 0.030" round hole die, ABA block copolymer of l-lactide A-block and TMC d,l-lactide (90/10) B-block with A and B approximately 50% the modified Instron as an extruder, fibers are extruded at 220° C. The fibers are further drawn close to the maximum and are held at that length to set. The fibers can be used as synthetic sutures.

2. Sutures and fibers from the above example can also be coated, multiplied or braided to be used in areas where higher mechanical strength, softer texture or better knot holding capability is desired.

EXAMPLE 13

Nerve Channel Extrusion

The fabrication of polycarbonates biopolymers to nerve channels, tubes, or hollow fibers based on l-lactide —TMC type of copolymers in an ABA or BAB triblock structure where A is l-lactide hard block and B, the rubbery block, is a copolymer of TMC with or without lactides, was evaluated using the Instron Rheometer as a ram extruder and a tube in orifice type die. The hollow fiber or tube dimensions were controlled by the die dimensions, differential gas pressure between the inner and outer surfaces of the tube, melt draw down and subsequent orientation processes. Range of diameters was about 0.5 to about 3 mm internal diameter, with significant wall thickness to provide rigidity and strength for implantation into an animal or human.

Dies having the outer diameters of the center tube of about 1.5 mm and orifices ranging from 2.5–3.5 mm were used without an appreciable applied pressure differential. There was significant die swell during extrusion which provided inner tube diameters greater than 3 mm. Other desirable diameters were easily achieved by drawing.

EXAMPLE 14

Nerve Channel Fabrication via Solution Dipping

Samples ranging from 0.5 mm I.D.×0.75 mm O.D. to 3.0 mm I.D.×3.50 mm O.D. were routinely prepared by this method for use as nerve channels.

a Mandrel materials included, e.g., Pyrex glass tubings or rods, stainless steel (316) tubings or rods, platinum wires and tungsten wires or rods. They were selected partly because of their higher surface energy so that the polymer solution would spread evenly on their surfaces and partly because they were relatively inert so they can be cleaned easily and reused.

b. Solvents: Usually tetrahydrofuran and a few drops methyl ethyl ketone or methyl isobutyl ketone. Occasionally, chloroform or 1,4-dioxane was used as the primary solvent depending on the solubility of the polymer system.

c. Polymer solutions ranging from 1% to 15% by weight to solvent volume ratio have been used and the concentration was adjusted so that between 8 to 20 dips would give the desirable wall thickness. (The rule of thumb is that the larger the diameter, the thicker the wall will be needed to avoid collapsing. Therefore, either more dips would be required or a slightly more concentrate solution could be used.)

d. Time between dips was usually ten to thirty minutes. For a few polymer systems, the wall contracted after overnight drying. Thus, an additional one or two dips had to be performed the following morning, i.e., 15 to 16 hours later.

e. Molecular weight of polymer used (weight average) generally ranged from 10,000 to 250,000, as determined by GPC in tetrahydrofuran and calibrated with polystyrene standards. No significant or detectable change of molecular weight was recorded with the polycarbonates used, before and after fabrication.

f. Most of the protheses were cut to the desired lengths while still on the mandrel. Before demandreling, the protheses were soaked in methanol or methanol/water or water for an hour in the refrigerator. This helped to remove the protheses off the mandrel and demandreling was performed in a Class 100 laminar flow hood and handled with clean room grade gloves.

g. Sterilization was generally performed with ethylene oxide at room temperature.

In this manner, nerve channels from random or block copolymers of TMC and lactides were prepared.

EXAMPLE 15

Tendon and Ligament Replacement Devices

Tendon and ligament replacement devices can be fabricated from these biopolymer fibers by the following techniques.

A. Uniaxial towed fiber device

A bundle of well aligned fibers roughly with cross-sectional dimensions of 5–6 mm by 0.4–0.5 mm and with a length of 45 cm are fastened onto two surgical needles. The device is cleaned with 0.05% Trinton X-100 in 50% ethanol-water, then rinsed six times with water, and finally rinsed with absolute alcohol. The operation is performed inside a class 100 laminar flow hood from the cleaning of the device up to and including packaging of the device in sterilization bags. Room temperature ethylene oxide is used to sterilize these devices.

The device of this size is useful for tendon or ligament replacements in small animals, e.g., the Achilles tendon in rabbits.

B. Coated uniaxial towed fiber devices

A bundle of 44 yarns of a 220 denier yarn, made from a 5 denier per filament fiber with tensile strength of 2.83 g/d and spun from a 98% DMTMC-2% TMC random copolymer, was cleaned by ultrasonic bath with 0.05% Triton X-100 water-ethanol solution. It was rinsed thoroughly in deionized water, and then with absolute alcohol. After air drying in a laminar flow hood, the yarn was coated with a 7% DMSO solution of 91% TMC-9% 1-lactide random copolymer of MW~87,000. The yarn was coated by dipping into the solution. After air drying (over 7 hrs.), it was inverted and dip coated for a second time. Coating weight gain was determined to be 6%. For insertion of the two ends of the prosthesis through the eye of the surgical needle, the ends were coated four more times with the solution so that the individual filaments cannot be readily separated. After thorough air drying, the prosthesis was placed in a sterilization pack and sterilized with ethylene oxides. The prothesis made was ready for rabbit Achilles tendon replacement.

C. Coated unaxial towed fiber devices

Similarly, a coated device of the 91% TMC 9% 1-lactide coating a high strength (extended chain) polyethylene fiber was constructed. A bundle of 14 Spectra 1000 medical grade extended chain polyethylene yarn (650 denier yarn) was cleaned and dried as above. A 0.3% tetrahydrofuran solution of the 91% TMC-9% 1-lactide copolymer was used for dip coating. Dip coating twice allowed a weight gain of 3% which was sufficient to have most of the filaments adhere together but the prothesis was not coated too heavily to become rigid and kink. The two ends were also coated extra for ready needle insertion. After air drying and sterilization with ethylene oxide, the prosthesis made was ready for replacing the rabbit Achilles tendon.

D. Braided and crocheted fabric devices

Six yarns of twisted fibers are braided together to form a strand of fabric 45mm in length and with cross-sectional dimensions of 1mm by 6mm. Similarly, yarns are crocheted into devices of various cross-sectional diameter and length, depending on the end application. These fabrics are cleaned as discussed above and are to be used as replacement devices for ligaments and tendons in small animals.

EXAMPLE 16

Nerve Channel

Implantation Studies

Mouse Sciatic Nerve Regeneration

Adult anesthetized C57BL/6J mouse with a sciatic nerve transected has both the proximal stump and distal stump secured by a single 10–0 nylon suture and inserted into a 5–6 mm length of a nerve channel tube made from the biopolymers of e.g. those from Example 3 or nerve channels made as in Example 19 to give a final gap length of 3–4 mm. Postoperatively, at 6 weeks, the sciatic nerve of the animal, appropriately perfused for tissue studies, is again exposed and retransected 3 mm distal to the nerve guide tube. Nerve guides with enclosed regerated nerves are then dissected out, post-fixed in 2% osmium tetroxide and processed for plastic embedding (DER, Ted Pella Inc.). Just before embedding, the tissue is usually divided into several segments for sampling at multiple cross-section levels. For most implants, five levels are sampled by one micron sections. These levels are: proximal sciatic stump at 1 to 2 mm proximal to the implant; three levels (proximal, central, distal) within the tube through the original gap, and the distal stump 1 to 2 mm distal to the implant. Data obtained in the central section is used for comparison.

The results will indicate that these channels do bioresorb and that they do not cause scar formation. They will be as much or more vasotropic than the poly d,1-lactide channels. In addition, the epineurium of the regenerated nerve using these nerve guides will be much thinner than that using the lactide guides and approximates the size of the intact nerve.

EXAMPLE 17

Assymetric Membrance From Block Copolymer

The ABA block copolymer of Example 3, Sample No. 2, was used to prepare the asymmetric membrane. A sample of the polymer (5 g) was dissolved in a mixture of tetrahydrofuran (35 mL) and diglyme (5 mL) and protected from drafts. The solvents were allowed to evaporate for about 4 hrs, then the plate was placed in an oven at 45°–50° C. overnight. The resulting film was removed from the plate and submitted for analysis by scanning electron microscopy. This showed that the film has a tight, smooth, non-porous side (the glass side), and a highly porous reverse side. Cross section of the film shows that there are many pores and channels thoroughout the bulk of the film except for the side of the tight skin. Films varying in thickness from about 80 to about 350 μm were prepared in this way.

EXAMPLE 18

Fabrication of Rod and Ribbon as Internal Support in Conjunction with Balloon Angioplasty An ABA block copolymer, e.g. those from Examples 21 or 22 is extruded at around 200° C. in the modified Instron extruder, with either a round or a rectangular die. The rod or ribbon produced is stored in a Class 100 laminar flow hood for over 48 hrs., before it is cold drawn. The product is wrapped around a 2 mm diameter glass rod as mandrel, in a spiral fashion, and stabilized at both ends. Dimethyl sulfoxide is added dropwise to the "spiral" while the mandrel was rotating at 5 RPM by a motor in a horizontal position. After several days, the product is removed from the mandrel. The spiral form of the product is retained. This type of completely bioresorbable "spring" can be used in conjunction with balloon angioplasty to help to maintain the patency of re-opened blood vessel, replacing clips or springs made of stainless steel or other materials.

EXAMPLE 19

Sample 2 from Example 3 was an ABA block copolymer with A:B ratio of 30:70 and with 1-LA (A block) and a 9 and 1 copolymer of TMC and d,1-LA (B block). Elastic tubes, useful as nerve channels, fallopian tube replacements, were extruded at 200° C. similar to Example 12. Whenever the tubes were deliberately pinched close, they would reopen immediately. Tube inner diameters of 0.5 to 3 mm were achieved.

EXAMPLE 20

Biopolymer Coated Polyurethane Devices

ComfaDerm KM-1422-00 (obtained from Semex Medical, Malvern, Pa., USA), a medical grade foamed, flexible polyurethane coated on one side with a pressure sensitive medical adhesive, was coated from the other side with a 4% DMSO solution of 90% TMC/10% 1-lactide random copolymer. Once the solution was applied evenly on the surface and subjected to 110° C. heating in an air oven, the solution soaked through the foam and, therefore coated the system, in a matter of minutes. Thorough drying for over 12 hrs afforded an evenly coated flexible foamed polyurethane based device.

Similarly, dimethylacetamide solution casted thin or thick films of polyurethane, e.g., Pellethane 2103–80AE and Pellethane X0119-70A (obtained from Upjohn Co.), were readily coated with a 4% DMSO biopolymer coating solution. Once the casted polyurethane film is casted, dried in an 120° C. oven, the DMSO coating solution was added onto the film while still hot. The solution had a tendency to adhere unevenly; however, with care in spreading the solution, and subjecting the system to heating in the oven, and repeating the spreading and heating cycle a few times over time, e.g., one hour, even coated surfaces were obtained. Strong adhesion was achieved as demonstrated by pin pricking and rubbing, which did not separate the two films.

EXAMPLE 21

ABA Block Copolymer of Trimethylene Carbonate (TMC), d,1-lactic Acdi (d,1-LA) [B-block] and 1-lactic Acid (1-LA) [A-block] Containing 45% TMC.

An oven-dried, silanized glass 100 mL resin flask is equipped with mechanical stirrer with a glass paddle, argon inlet, a serum cap on one port, and a glass stopper on the remaining port. To the flask are added freshly dried and purified TMC (22.5 g, 220 mmol), d,1-lactide (2.25 g, 17.3 mmol) and 1,6-hexanediol (25 mg, 0.21 mmol). The flask is evacuated and filled with argon several times, then immersed in an oil bath at 150° C. Stirring is initiated, and after 5 mins., 30 μL of a 0.20M solution of stannous octoate in toluene is added.

After 2.5 hrs., a sample of the viscous polymer is removed and 1-lactide (25.0 g, 173 mmol) is added through one port. Stirring is stopped after 3 hrs., then heating stopped after an additional hour. The polymer is removed from the flask, dissolved in tetrahydrofuran (250 mL), precipitated into methanol (750 mL), and dried under vacuum at 50° C.

EXAMPLE 22

ABA Block Copolymer Trimethylene Carbonate (TMC) [B-block] and l-Lactic Acid (l-LA) [A-block] Containing 50% TMC.

An oven-dried, silanized glass 100 mL resin flask is equipped with mechanical stirrer with a glass paddle, argon inlet, a serum cap on one port, and a glass stopper on the remaining port. To the flask are added freshly dried and purified TMC (25.0 g, 245 mmol) and 1,6-hexanediol (25 mg, 0.21 mmol). The flask is evacuated and filled with argon several times, then immersed in an oil bath at 150° C. Stirring is initiated, and after 5 mins., 30 μL of a 0.20M solution of stannous octoate in toluene is added.

After 2.5 hrs., a sample of the viscous polymer is removed and l-lactide (25.0 g, 173 mmol) is added through one port. Stirring is stopped after 3 hrs., then heating stopped after an additional hour. The polymer is removed from the flsk, dissolved in tetrahydrofuran (250 mL), precipitated into methanol (750 mL), and dried under vacuum at 50° C.

What is claimed is:

1. A medical device formed totally or in part of one or more random copolymers having at least one type of recurring monomeric unit of the General Structure I:

$$\text{Structure I} \quad +O-\underset{\underset{H}{|}}{\overset{\overset{H}{|}}{C}}+\underset{\underset{H}{|}}{\overset{\overset{H}{|}}{C}}\!\!\!+_{n}\!\!\!\underset{}{C}-O-\overset{\overset{O}{\|}}{C}+$$

and having at least one type of recurring monomeric unit of the Structure II:

$$\text{Structure II} \quad +\underset{\underset{R_2}{|}}{\overset{\overset{R_1}{|}}{C}}-\overset{\overset{O}{\|}}{C}O+$$

wherein:
n is from 1 to about 8; and
$R_1$ and $R_2$ are the same or different and are hydrogen, alkyl or phenyl.

2. A medical device according to claim 1 wherein n is 1 to about 3.

3. A medical device according to claim 2 wherein n is 1.

4. A medical device according to claim 1 wherein $R_1$ and $R_2$ are the same or different and are hydrogen or alkyl.

5. A medical device according to claim 4 wherein $R_1$ and $R_2$ are the same or different and are hydrogen or alkyl having from 1 to about 4 carbon atoms.

6. A medical device according to claim 5 wherein the recurring monomeric units of the Structure II are derived from a lactide.

7. A medical device according to claim 6 wherein the recurring monomeric units of the Structure II are derived from d-lactide, l-lactide or d,l-lactide.

8. A medical device according to claim 1 wherein the amount of the recurring monomeric units of the Structure I in said copolymer is at least about 75 wt. % based on the total weight of recurring monomer units.

9. A medical device according to claim 8 wherein said amount is at least about 85 wt %.

10. A medical device according to claim 9 wherein said amount is from about 85 % to about 99 wt %.

11. A medical device according to claim 10 wherein said amount is from about 90 wt % to about 99 wt %.

12. A medical device according to claim 1 wherein said device further comprises a biodurable portion.

13. A medical device according to claim 12 wherein said copolymer coats all or a portion of said biodurable portion.

14. A medical device according to claim 1 which further comprise one or more other bioresorbable polymers.

15. A medical device according to claim 14 wherein said copolymer coats all or a portion of said bioresorbable polymer.

16. A medical device according to claim 1 which is a vascular graft.

17. A medical device according to claim 1 which is a wound closing or covering device.

18. A medical device according to claim 1 which is a nerve channel.

19. A random copolymer having at least one type of recurring monomeric unit of the Structure I:

$$\text{STRUCTURE I} \quad +O-\underset{\underset{H}{|}}{\overset{\overset{H}{|}}{C}}+\underset{\underset{H}{|}}{\overset{\overset{H}{|}}{C}}\!\!\!+_{n}\!\!\!\underset{}{C}-O-\overset{\overset{O}{\|}}{C}+$$

and having at least one type of recurring monomeric unit of the Structure II:

$$\text{STRUCTURE II} \quad +\underset{\underset{R_2}{|}}{\overset{\overset{R_1}{|}}{C}}-\overset{\overset{O}{\|}}{C}O+$$

wherein:
n is from 1 to about 8; and
$R_1$ and $R_2$ are the same or different and are hydrogen, alkyl or phenyl.

20. A random copolymer according to claim 19 wherein n is 1 to about 3.

21. A random copolymer according to claim 20 wherein n is 1.

22. A random copolymer according to claim 19 wherein $R_1$ and $R_2$ are the same or different and are hydrogen or alkyl.

23. A random copolymer according to claim 22 wherein $R_1$ and $R_2$ are the same or different and are hydrogen or alkyl having from 1 to about 4 carbon atoms.

24. A random copolymer according to claim 23 wherein the recurring monomeric units of the Structure II are derived from a lactide.

25. A random copolymer according to claim 24 wherein the recurring monomeric units of the Structure II are derived from d-lactide, l-lactide or d,l-lactide.

26. A random copolymer according to claim 19 wherein the amount of the recurring monomeric units of the Structure I in said copolymer is at least about 75 wt. % based on the total weight of recurring monomer units.

27. A random copolymer according to claim 26 wherein said amount is at least about 85 wt. %.

28. A random copolymer according to claim 27 wherein said amount is from about 85 wt. % to about 99 wt. %.

29. A random copolymer according to claim 28 wherein said amount is from about 90 wt. % to about 99 wt. %.

30. The device of claim 1 wherein the amount of recurring monomeric units of the structure I in said copolymer is more than about 50 weight % based on the total weight of all recurring monomeric units in the copolymer.

31. The device of claim 1 wherein the amount of recurring monomeric units of the Structure II in said copolymer is more than about 50 weight % based on the total weight of all recurring monomeric units in said copolymer.

32. The device according to claim 31 wherein the amount of the recurring monomeric units of the Structure II in said copolymer is at least bout 75 wt. % based on the total weight of recurring monomer units.

33. The device according to claim 32 wherein said amount is at least about 85 wt. %.

34. The device according to claim 33 wherein said amount is from about 85 wt. % to about 99 wt. %.

35. The device according to claim 34 wherein said amount is from about 90 wt. % to about 99 wt. %.

36. The device of claim 1 wherein at least one of $R_1$ and $R_2$ is other than hydrogen.

37. The device of claim 36 wherein:
n is 1;
$R_1$ is hydrogen; and
$R_2$ is methyl.

38. The random copolymer of claim 19 wherein at least one of $R_1$ and $R_2$ is other than hydrogen.

39. The random copolymer of claim 38 wherein:
n is 1;
$R_1$ is hydrogen; and
$R_2$ is methyl.

40. The random copolymer of claim 19 wherein the amount of recurring monomeric units of the structure I in said copolymer is more than about b 50 weight % based on the total weight of all recurring monomeric units in the copolymer.

41. The random copolymer of claim 19 wherein the amount of recurring monomeric units of Structure II in said copolymer is more than 50 weight % based on the total weight of all recurring monomeric units in the copolymer.

42. A random copolymer according to claim 41 wherein the amount of the recurring monomeric units of the Structure II in said copolymer is at least about 75 wt. % based on the total weight of recurring monomer units.

43. A random copolymer according to claim 42 wherein said amount is at least about 85 wt. %.

44. A random copolymer according to claim 43 wherein said amount is from about 85 wt. % to about 99 wt. %.

45. A random copolymer according to claim 44 wherein said amount is from about 90 wt. % to about 99.%.

46. A device according to claim 1 wherein:
n is 1; and
$R_1$ and $R_2$ are hydrogen.

47. A random copolymer of claim 19 wherein:
n is 1; and
$R_1$ and $R_2$ are hydrogen.

* * * * *